(12) United States Patent
Banchereau et al.

(10) Patent No.: US 7,615,212 B2
(45) Date of Patent: Nov. 10, 2009

(54) COMPOSITIONS AND METHODS FOR THE SYSTEMIC TREATMENT OF ARTHRITIS

(75) Inventors: Jacques Banchereau, Dallas, TX (US); Virginia Pascual, Dallas, TX (US)

(73) Assignee: Baylor Research Institute, Dallas, TX (US)

( * ) Notice: Subject to any disclaimer, the term of this patent is extended or adjusted under 35 U.S.C. 154(b) by 185 days.

(21) Appl. No.: 11/067,335

(22) Filed: Feb. 25, 2005

(65) Prior Publication Data

US 2005/0192241 A1 Sep. 1, 2005

Related U.S. Application Data

(60) Provisional application No. 60/548,033, filed on Feb. 26, 2004.

(51) Int. Cl.
*A61K 39/395* (2006.01)
*A61K 38/20* (2006.01)
(52) U.S. Cl. .................. 424/130.1; 514/2; 514/12; 514/825; 530/351; 530/387.1; 530/389.1
(58) Field of Classification Search .............. None
See application file for complete search history.

(56) References Cited

U.S. PATENT DOCUMENTS

| | | | |
|---|---|---|---|
| 5,350,683 A | 9/1994 | Sims et al. | |
| 5,747,072 A | 5/1998 | Davidson et al. | |
| 5,780,513 A | 7/1998 | McDaniel et al. | |
| 5,922,573 A | 7/1999 | Boraschi et al. | |
| 6,096,728 A | 8/2000 | Collins et al. | |
| 6,121,266 A | 9/2000 | Dolle et al. | |
| 6,159,460 A | 12/2000 | Thompson et al. | |
| 6,197,551 B1 | 3/2001 | Busfield | |
| 6,204,261 B1 | 3/2001 | Batchelor et al. | |
| 6,268,142 B1 | 7/2001 | Duff et al. | |
| 6,413,511 B1 | 7/2002 | Glorioso et al. | |
| 6,573,366 B1 | 6/2003 | Zanette et al. | |
| 6,599,873 B1 | 7/2003 | Sommer et al. | |
| 6,710,084 B2 | 3/2004 | Serhan | |
| 7,037,492 B2 | 5/2006 | Glorioso et al. | |
| 7,067,144 B2 | 6/2006 | Demopulos et al. | |
| 7,192,917 B2 | 3/2007 | Tracey et al. | |
| 7,446,175 B2 | 11/2008 | Gram et al. | |
| 2001/0053764 A1* | 12/2001 | Sims et al. ............ | 514/12 |

2003/0235890 A1    12/2003   Wyllie et al.

OTHER PUBLICATIONS

Fredericks et al. *Protein Engineering, Design & Selection*, vol. 17, pp. 95-106, Jan. 2004.*
De Benedetti, F., et al., 1991, "Correlation of Serum Interleukin-6 Levels with Joint Involvement and Thrombocytosis in Systemic Juvenile Rhematoid Arthritis," Arthritis Rheum 34:1158-1163.
De Benedetti, F., et al., 1992. "Serum Interleukin-6 Levels and Joint Involvement in Polyarticular and Pauciarticular Juvenile Chronic Arthritis," Clin Exp Rheumatol 10:493-498.
De Benedetti, F., et al., 1995. "Circulating levels of interleukin 1β and of interleukin 1 receptor antagonist in systemic juvenile chronic arthritis," Clin Exp Rheumatol 13:779-84.
Frankel, A.E., et al. 2001. "Novel Therapeutics for Chemotherapy-Resistant Acute Myeloid Leukaemia," BioDrugs 15:55-57.
Hull, K.M., et al., 2003, "The Expanding Spectrum of Systemic Autoinflammatory disorders and Their Rheumatic Manifestations," Curr Opin Rheumatol 15:61-69.
Ideo, G. and Bellobuono, A., 2002. "New Therapies for the Treatment of Chronic Hepatitis C," Curr Pharm Des 8:959-966.
Kaplanski, G., et al.1994. "Interleukin-1 Induces Interleukin-8 Secretion from Endothelial Cells by a Juxtacrine Mechanism," Blood 84:4242-4248.
Kwon, et al., 2004, "Suppressive Effects of Natural and Synthetic Agents on Dexatran Sulfate Sodium-induced Interleukin-1 β from Murine Peritoneal Macrophages," Biosci. Biotechnol. Biochem. 68 (2):436-437.
Lorenz, H.M. and Kalden J.R., 2001. "Neue Therapieentwicklungen in der Rheumatoiden Arthritis," Z Rheumatol 60:326-32.
Mangge, H, et al., "Long-Term Follow-Up of Cytokines and Soluble Cytokine Receptors in Peripheral Blood of Patients with Juvenile Rheumatoid Arthritis," 1999. J Interferon Cytokine Res 19:1005-1010.
Mehta, R.C., et al. 2000. "Intercellular Adhesion Molecule-1 Suppression in Skin by Topical Delivery of Anti- Sense Oligonucleotides," J Invest Dermatol 115):805-812.
Muller, K, et al. "Inflammatory Cytokines and Cytokine Antagonists in Whole Blood Cultres of Patients with Systemic Juvenile Chronic Arthritis," 1998. Br J Rheumatol 37:562-569.

(Continued)

*Primary Examiner*—Jeffrey Stucker
*Assistant Examiner*—Stephen Gucker
(74) *Attorney, Agent, or Firm*—Chainey P. Singleton; Edwin S. Flores; Chalker Flores, LLP (57) ABSTRACT

The present invention includes compositions and methods for treating arthritic joints found in patients with autoinflammation, e.g., systemic onset juvenile idiopathic arthritis, by administering at the site of inflammation a therapeutically effective amount of at least one agent that reduces or blocks the bioavailability of interleukin-1β.

4 Claims, 4 Drawing Sheets

OTHER PUBLICATIONS

Muzaffer, M., et al., 2002, "Differences in the Profiles of Circulating Levels of Soluble Tumor Necrosis Factor Receptors and Interleukin 1 Receptor Antagonist Reflect the Heterogeneity of the Subgroups of Juvenile Rheumatoid Arthritis," J Rheumatol 29:1071-1078.

Ozen, S, et al. 1997, "Interleukin-1, -6, and -8 Levels in Juvenile Chronic Arthritis," Clin Rheumatol 16:173-178.

Sandborn, W.J. And Targan, S.R., 2002. "Biologic Therapy of Inflammatory Bowel Disease," Gastroenterology 122:1592-1608.

Serhan, C.N. and Clish, C.B., 2002, "Aspirin Triggered Lipid Mediators: Novel inhibitors of Leucocyte Trafficking," Thorax, 55:S10-S12.

Shahin, A., et al., "Circulating interleukin-6, soluble interleukin-2 receptors, tumor necrosis factor alpha, and interleukin-10 levels in juvenile chronic arthritis: correlations with soft tissue vascularity assessed by power Doppler sonography," 2002. Rheumatol Int 22:84-88.

Yokata, S. 2003. "Interleukin 6 as a herapeutic target in systemic-onset juvenile idiopathic arthritis," Curr Opin Rheumatol 15:581-586.

International Search Report and Written Opinion for PCT/US2005/006200 dated Oct. 31, 2005.

Nuki, G., et al., "Long-Term Safety and Maintenance of Clinical Improvement Following Treatment with Anakinra (Recombinant Human Interleukin-1 Receptor Antagonist) in Patients with Rheumatoid Arthritis," Arthritis and Rheumatism (2002), 46:2838-2846.

* cited by examiner

FIGURE 3C WBC

FIGURE 3D HEMOGLOBIN

FIGURE 3E PLATELETS

FIGURE 3F ESR

COMPOSITIONS AND METHODS FOR THE SYSTEMIC TREATMENT OF ARTHRITIS

REFERENCE TO RELATED APPLICATION

This application claims priority to U.S. Provisional Patent Application Ser. No. 60/548,033, filed Feb. 26, 2004, the entire content of which is incorporated herein by reference.

TECHNICAL FIELD OF INVENTION

The present invention relates to therapeutic use of a bio-affecting and body-treating composition, and more particularly, to compositions and methods for the systemic treatment of joint inflammation.

BACKGROUND OF THE INVENTION

Juvenile idiopathic arthritis ("JIA"), also referred to as juvenile rheumatoid arthritis ("JRA") or juvenile chronic arthritis ("JCA") is the most common rheumatic disease in childhood and an important cause of both short and long-term disability. The term "JIA" includes a heterogeneous group of diseases, each of which may have a variety of causes and elicit a variety of host responses. All are characterized, however, by the development of idiopathic peripheral arthritis thought to be secondary to an immuno-inflammatory pathogenesis, possibly triggered by contact with external antigen(s). JIA is classified according to three major types of disease presentation: (1) oligoarthritis; (2) polyarthritis; and (3) systemic onset juvenile idiopathic arthritis (hereinafter "SOJIA"). Each of these groups is defined by a constellation of clinical signs and symptoms during the first six months of illness.

Of the known JIA diseases, all three major groups based on primary modes of onset have been considered to: (1) have an "autoimmune etiology"; and (2) follow a complex, nonmendelian, genetic trait. Evidence of underlying autoimmunity is mainly drawn from the presence of autoantibodies and/or immune complexes in the patient's sera. Anti-nuclear antibodies occur in a high proportion of children with oligoarticular and, to a lesser extent, polyarticular onset, and these antibodies confer a higher risk of developing uveitis. Other autoantibodies directed against cytoplasmic and extracellular components such as collagen have also been described. Rheumatoid factors (RF) are detected in approximately 3% of children with JIA, and the presence of these autoantibodies defines a subgroup of polyarticular onset patients whose disease is undistinguishable from adult onset rheumatoid arthritis (Cassidy, J T and Ross, E. 2001. *Textbook of Pediatric Rheumatology*, 4th ed, Books on Demand Publishers, Visby, Sweden; p. 218-321).

A variety of T cell alterations have been described mainly in the blood and synovial fluid of children with oligoarthritis, but a consistent pattern of cytokine production has not been found. In both oligoarthritis and polyarthritis patients, increased soluble IL-2R and IL-1β have been found in the blood. In all three forms of JIA, TNF-α and soluble TNFαR (p55/75) have been found elevated in the serum and/or synovial fluid (SF). In SOJIA patients, abnormal expression of IL-6 has been described, especially in the blood prior to the febrile spikes, and IL-6 levels correlate with the systemic activity of the disease, with the development of arthritis, and with the increase in acute phase reactants (Yokata, S. 2003. "Interleukin 6 as a therapeutic target in systemic-onset juvenile idiopathic arthritis," *Curr Opin Rheumatol* 15:581-586). IL-6 deregulation has also been proposed to mediate the linear growth retardation, thrombocytosis and anemia seen in SOJIA patients (de Benedetti F, et al., 1991. *Arthritis Rheum* 34:1158-1163; Mangge H, et al. 1999. *J Interferon Cytokine Res* 19:1005-1010; Ozen S, et al. 1997. *Clin Rheumatol* 16:173-178; de Benedetti F, et al., 1999. *J Rheumatol* 26:425-431; Muller K, et al. 1998. *Br J Rheumatol* 37:562-569; Shahin A, et al., 2002. *Rheumatol Int* 22:84-88; de Benedetti F, et al., 1992. *Clin Exp Rheumatol* 10:493-498; and Muzaffer M, et al., 2002. *J Rheumatol* 29:1071-1078).

Data on HLA segregation suggests a hereditary basis to the complex etiopathogenesis of the disease(s) in cases of oligoarticular and polyarticular onset JIA. Studies in SOJIA have yielded, however, inconsistent results. Finally, both viruses and bacteria have been described in association with chronic arthritis in children. Rubella and Parvovirus B19 can cause chronic arthritis secondary to persistence of the organism or by triggering an immune reaction, as it has also been described in cases of post-vaccination arthritis.

SOJIA represents about 10% of all the cases of JIA. The course and prognosis of SOJIA is heterogeneous, as fifty percent of patients have a monophasic course with resolution of the symptoms, while the remaining fifty percent develop a chronic relapsing and remitting course and a very severe form of polyarticular chronic arthritis. Patients with SOJIA also display an increased risk of developing hemophagocytic syndrome, a potentially fatal complication (Cassidy, J T and Ross, E. 2001. *Textbook of Pediatric Rheumatology*, 4th ed, Books on Demand Publishers, Visby, Sweden; p. 218-321).

Children with SOJIA present with severe systemic symptoms (fever and rash) that usually precede the development of arthritis for weeks to years. The high spiking fever, which is the hallmark of this disease, usually follows a quotidian pattern with 1-2 spikes/day. Patients look characteristically well when the fever is not present, but become quite ill with the spikes. In many patients, the fever is accompanied by a salmon-pink rash that becomes more apparent with the fever. Additionally, children with SOJIA may have hepatosplenomegaly, lymphadenopathy, pericarditis and other manifestations of serositis. These systemic manifestations may last from weeks to months and eventually tend to subside to be followed by the development of chronic arthritis. About 50% of patients will present oligoarticular involvement and will eventually recover. The other half will evolve into a polyarticular pattern, the prognosis of which correlates with the number of joints involved six months into the disease course. Up to 48% of children with SOJIA will have active arthritis ten years after the diagnosis is made (Cassidy, J T and Ross, E. 2001. *Textbook of Pediatric Rheumatology*, 4th ed, Books on Demand Publishers, Visby, Sweden; p. 218-321; and Lomater C, et al., 2000. *J Rheumatol* 27:491-496).

There are no available specific tests to establish the diagnosis of SOJIA, nor are there known prognostic indicators to ascertain its clinical course. Fever, anemia, leukocytosis and elevated erythrocyte sedimentation rate (ESR) are the main initial features of the disease, sometimes lasting several months before the diagnosis can be established. As these symptoms are nonspecific and can mimic infections, malignancies, and other diseases, patients undergo a series of very costly diagnostic tests and prolonged hospitalizations.

One of the most serious complications in patients with SOJIA is the development of hemophagocytic syndrome, also known as macrophage activation syndrome (MAS) (Cassidy, J T and Ross, E. 2001. *Textbook of Pediatric Rheumatology*, 4th ed, Books on Demand Publishers, Visby, Sweden; p. 218-321). The hemophagocytic syndrome, which can occur as well in the context of infectious and neoplastic diseases, is associated with serious morbidity and/or death. Its etiology, especially in the context of SOJIA, is unknown.

Familial cases of MAS occur as the result of defective viral killing due to mutations in genes like perforin (involved in the release of granzyme by cytotoxic T cells/natural killer cells to target cells) or Rab27 (involved in the control of granzyme vesicle degranulation).

SUMMARY OF THE INVENTION

Therefore, SOJIA remains a chronic inflammatory disease of unknown etiology for which a specific treatment has not been determined. Despite extensive study, multi-drug treatment of patients with SOJIA is similar to that of oligoarthritis and polyarthritis, which depends on the phase (systemic phase versus arthritic phase) of the disease and on the extent of involvement. While a minority of patients does well with non-steroidal anti-inflammatory drugs (NSAIDs), most children require the use of oral and/or parenteral steroids as well as methotrexate to control the symptoms. Intravenous immunoglobulin (IVIG) has been used in recalcitrant cases. Most recently, anti-TNF therapy (e.g., etanercept and infliximab) is being added to these regimens. Nevertheless, there are some limitations and risks associated with these drugs. For example, long term treatment of these patients with immunosuppressive drugs such as methotrexate and steroids have been reportedly associated with an impaired ability of the patients to eliminate viral infections. Intravenous immunoglobulin treatment is accompanied by the risks associated with transfusions of blood-derived products. The present inventors have found that SOJIA patients do not respond as well and require higher doses of anti-TNF agents to control the symptoms than any other type of JIA. Therefore, there is a continuing need to identify effective drug treatments for SOJIA disease.

Blocking IL-1 has been reported as an effective agent for treating patients with inflammatory arthritis associated with autoimmune diseases. Clinical studies have been preformed on adults with rheumatoid arthritis and children with diverse forms of juvenile arthritis. Anakinra (Kineret®, made by Amgen), the recombinant human IL-1 receptor antagonist has the ability to block the interaction of IL-1 with its receptor, thus blocking the cellular response of IL-1. A clinical trial using Anakinra has been conducted with patients with severe rheumatoid arthritis. At 150 mg per day, a 43% response rate based on the American College of Rheumatology index was seen in comparison to 27% in placebo group. Clinical studies using IL-1 antagonists, however, have never been done in children or adults with Systemic Onset Arthritis during the systemic phase of the disease, as defined by the presence of fever and/or rash with or without arthritis. Furthermore, IL-1 has been reported not to play a relevant role in SOJIA disease (de Benedetti F, et al., 1995. "Circulating levels of interleukin 1 beta and of interleukin 1 receptor antagonist in systemic juvenile chronic arthritis," Clin Exp Rheumatol 13:779-84).

Autoinflammatory diseases are illnesses associated with alterations of the innate immune system. Cells of the innate immune system, e.g., neutrophils, monocytes, macrophages and NK cells, are characterized by the lack of somatically generated receptors, the clonal expansion of antigen-specific cells and their inability to confer "immunological memory." Although autoinflammatory diseases may clinically mimic autoimmune diseases, patients with autoinflammation never develop autoantibodies, which are the hallmark of many autoimmune diseases. On the other hand, most autoinflammatory diseases cause fever, usually with an intermittent or periodic pattern, and the skin and joints are frequently the targets of inflammation. In the past five years, the genes responsible for at least nine familial autoinflammatory diseases have been described. These include Familial Mediterranean Fever (FMF), Tumor Necrosis Factor-Associated Periodic Fever Syndrome (TRAPS), Hyper IgD, Cyclic Neutropenia, Familial Cold Urticaria (FCU), Muckle-Wells Syndrome, Chronic Inflammatory Neurologic and Articular Syndrome (CINCA), Familial Granulomatous Disease (Blau's Syndrome), and Crohn's disease (reviewed in Hull K M, et al., 2003. *Curr Opin Rheumatol* 15:61-69). Although most autoinflammatory diseases are the result of single gene mutations, there are some that follow complex genetic traits, like ulcerative colitis and some forms of Crohn's disease, and yet some, like Behcet's, that may not be genetic in origin.

Despite reports the contrary, the present inventors have found that SOJIA is an autoinflammatory disease and reducing or blocking the bioavailability of interleukin-1 beta (IL-1β) is an effective therapeutic treatment for SOJIA patients. In one aspect, the present invention is a method for treating a patient with systemic onset juvenile idiopathic arthritis by administering to the patient a composition with an effective amount of at least one agent capable of reducing or blocking the bioavailability of interleukin-1 beta.

More particularly, the present invention includes compositions and method for treating a joint undergoing autoinflammation, e.g., having systemic onset juvenile idiopathic arthritis, by administering to the joint a composition that includes a therapeutically effective amount of one or more active agents that reduces the bioavailability of interleukin-1β. The active agent may modify the transcription of the interleukin-1β gene or the translation of the interleukin-1β gene. Alternatively, the active agent may be a single-stranded RNA molecule, a double-stranded RNA molecule, an antisense RNA molecule, a small inhibitory RNA (siRNA) molecule, or an inhibitory RNA molecule (RNAi) designed to reduce the expression of interleukin-1β. Another active agent may block IL-1β receptors, e.g., an interleukin-1 receptor antagonist protein or peptide that blocks the interaction between IL-1β and the IL-1β receptor.

Yet another active agent modifies the release of IL-1β or an antibody to an IL-1β to reduce or neutralize IL-1β, or even an IL-1β receptor. In one specific example, the active agent may be a naturally occurring IL-1 receptor antagonist provided at between about 1, 10, 15, 25, 50, 100, 125, 150, 175, 200 and even 250 mg per day. Often doses may be halved for pediatric patients. The active agent may also be a single-stranded RNA molecule, a double-stranded RNA molecule, an antisense RNA molecule, a small inhibitory RNA (siRNA) molecule, or an inhibitory RNA molecule (RNAi) designed to target and reduce the expression of interleukin-1β receptor. Examples of active agents that affect or inhibit the release of IL-1β include anion transport inhibitors, e.g., lipoxins, and alpha-tocopherol. Other examples include opioids that inhibit a proteolytic enzyme that converts the inactive IL-1β precursor to its mature, active form. Yet other examples include antibodies that neutralize the biological function of IL-1β.

Yet another example of the present invention is a method for treating a patient with systemic onset juvenile idiopathic arthritis by administering to the patient a composition having an effective amount of at least one agent capable of reducing or blocking the bioavailability of an interleukin-1β. The composition may include an effective amount of at least one agent capable of reducing or blocking the bioavailability of an interleukin-1β receptor. For example, a composition for treating SOJIA includes a therapeutically effective amount of one or more active agents adapted for delivery to a joint that reduces the inflammation of the joint affected with SOJIA. The composition helps reduce one or more of the following symptoms: fever, rash, arthritis and white blood cell count of a SOJIA patient. The composition may include one or more active agents that are: modifiers of interleukin-1 beta (IL-1β) gene transcription; modifiers of IL-1β gene translation; siRNAs that target the expression of IL-1β; IL-1β receptors blockers; interleukin-1 receptor antagonist proteins; interleukin-1 receptor antagonist peptides; active agents that modify the release of IL-1β; antibodies that neutralize IL-1β; antibodies that blocks an IL-1β, receptor; recombinant, naturally occurring IL-1 receptor antagonists; anion transport inhibitors, lipoxins and alpha-tocopherol that inhibit the release of IL-1β; opioids that inhibits a proteolytic enzyme that converts the inactive IL-1β precursor to its mature, active form; antibodies that neutralizes the biological function of IL-1β, and mixtures or combinations thereof. The pharmaceutical formulation may be adapted to treat joint autoinflammation and may be a made available in a variety of dosage forms, including, intravenous, intramuscular, oral, nasal, rectal, peritoneal, sub-cutaneous, intra-cutaneous (e.g., a patch), and the like.

The present invention also include a method of monitoring a therapeutic response to an autoinflammatory disease, e.g., SOJIA by monitoring the fever, rash, arthritis, white blood cell count and/or the sedimentation rate of white blood cells after treatment using the methods and compositions taught and disclosed herein. The present invention will find utility in a wide variety of contexts, e.g., treating an animal suffering from an autoinflammation by administering a therapeutic agent to an animal suffering from autoinflammation, wherein that agent including an antagonist of Interleukin 1β function in a pharmaceutically acceptable carrier, wherein the antagonist suppresses the autoinflammation.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. As used in the claim(s), in conjunction with the word "comprising," the words "a" or "an" may mean one or more than one. As used herein, "another" may mean at least a second or more of an item. The terminology herein is used to describe specific embodiments of the invention, but their usage does not delimit the invention, except as outlined in the claims.

As used herein, the term the "therapeutically effective" is used to define the amount of a compound required to improve some symptom associated with autoinflammatory disease, e.g., SOJIA. For example, in the treatment of autoinflammation, the present invention includes one or more active agents that improve the health or movement of a joint to any degree or arrests any symptom of a joint disease would be therapeutically effective. A therapeutically effective amount of a compound is not required to cure a disease but will provide a treatment for a disease.

As used herein, the phrase "a therapeutically effective amount of one or more active agents that reduces the bioavailability of interleukin-1β" is the amount of an inhibitor of IL-1β expression, translation, processing, release or activity; an inhibitor of IL-1β receptor expression, translation, processing, release or activity; and/or inhibitors of second messenger(s) expression, translation, processing, release or activity that are downstream from the IL-1β receptor when administered at, to or about a joint, or to an animal systemically or locally, that reduced the scope and extent of autoinflammation.

As used herein the term, "interleukin-1β receptor" is used to describe the cognate receptor for interleukin-1β. Non-limiting examples of agents that may specifically bind to, whether causing activation of the receptor or not, include: interleukin-1β, anti-interleukin-1β receptor antibodies or fragments thereof, peptides, proteins, glycoproteins, lipoproteins, epitopes, lipids, lectins, carbohydrates, multi-molecular structures, and specific conformation of one or more molecules. A "receptor" is a naturally occurring molecule or complex of molecules that is generally present on the surface of cells of a target organ, tissue or cell type, e.g., a joint.

As used herein the term "modify" or "modifies" is meant to include up or down regulation of the function of a gene or gene product, e.g., affecting the transcription, translation, processing, release or modification of a gene or gene product. The active agent may modify the transcription of the interleukin-1β gene. Examples of modification include, e.g., transcriptional or post-transcriptional silencing, changes to message stability and the like. Examples of post-translational modifications include maturation of the gene product or protein, post-translational modifications (e.g., glycosylation, disulfide bonding, myristylation, protease cleavage, association with other proteins, ubiquitination, etc.). The processing, transport and release of the protein may also be modified, e.g., by placing in storage organelles prior to release, by association with other proteins that affect release and the like.

The present inventors have recognized that SOJIA is an autoinflammatory disease rather than an autoimmune disease. Therefore, one aspect of the present invention is treatment of SOJIA aimed at targeting the cells (and the cell products) of the innate immune system rather than the adaptive immune system.

According to the present invention, IL-1β has now been found to be a fundamental mediator of inflammation in "autoinflammatory" diseases. Moreover, IL-1β modulation can be effective in treatment of autoinflammatory diseases including but not limited to SOJIA.

In one embodiment of the invention the formulation will include a therapeutically effective amount of one or more IL-1 inhibitors, such as type I or type II IL-1 receptor (e.g., IL-1 binding fragments of type II IL-1 receptor, see e.g., U.S. Pat. No. 5,350,683, relevant portions incorporated herein by reference); IL-1 binding and IL-1 inhibitory fragments of type I IL-1 receptor; IL-1 receptor antagonist, IL-1 beta converting enzyme (ICE) inhibitors, antibodies to IL-1, including IL-1 alpha and IL-1 beta and other IL-1 family members, and therapeutics known as IL-1 traps and antagonistic type I IL-1 receptor antibodies. Other specific IL-1 inhibitors for use with the present invention include IL-1 RA and variants or fragments thereof (see e.g., U.S. Pat. No. 5,922,573, relevant portions incorporated herein by reference). Yet another active agent is an IL-1 beta converting enzyme (ICE) inhibitor, e.g., peptidyl and small molecule ICE inhibitors including those described in PCT patent application WO 93/16710; and European patent application 0 547 699, relevant portions incorporated herein by reference). Non-peptidyl compounds (see e.g., U.S. Pat. No. 6,121,266, relevant portions incorporated herein by reference) and ICE (see e.g., U.S. Pat. No. 6,204,261, relevant portions incorporated herein by reference). Other IL-1 antagonists include chimeric proteins that include portions of both an antibody molecule and an IL-1 antagonist molecule, chimeras and multimers thereof, and IL-1 antagonists such as peptides derived from IL-1 that are capable of binding competitively to the IL-1 signaling receptor, IL-1 RI and/or IL-1 RI.

In particular, it has now been found that administering an agent to significantly reduce or effectively block the bioavailability of interleukin-1 beta (IL-1β) is a therapeutic option for SOJIA patients. As used herein, significant reduction of the bioavailability of IL-1β is defined as a sufficient reduction of bioavailable IL-1β to effect a reduction in symptoms and/or disease progression in SOJIA patients. In the present invention, at least one agent capable of significantly reducing or effectively blocking the bioavailability of IL-1β is administered to a patient diagnosed with SOJIA to effect a reduction in symptoms and disease progression. It is contemplated that more than one agent capable of reducing or blocking the bioavailability of (IL-1β) can be administered to an SOJIA patient either concomitantly or sequentially. It is further contemplated that one or more agents capable of reducing or blocking the bioavailability of (IL-1β) can be administered to an SOJIA patient in combination with other drug treatments either concomitantly or sequentially.

Techniques and compositions for making useful dosage forms using the present invention are described in one or more of the following references: United States Pharmacopeia (USP #24 NF19) (Hardcover Text w/3 Supplements)(United States Pharmacopeial 2002). Remington: The Science and Practice of Pharmacy, (21st Edition, formerly, Remington's Pharmaceutical Sciences), Mack Publishing Co, 2005); Advances in Pharmaceutical Sciences (David Ganderton, Trevor Jones, Eds., 1992), and the like, relevant portions incorporated herein by reference.

Generally, the therapeutic formulations of the present invention will be provided to a person in need of preventive or therapeutic intervention in water, a suitable oil, saline, aqueous dextrose (e.g., glucose, lactose and related sugar solutions) and glycols (e.g., propylene glycol or polyethylene glycols) or other suitable carriers for intravenous or parenteral administration. Solutions for parenteral administration include generally, a water soluble salt of the active ingredient, suitable stabilizing agents, and if necessary, buffering salts. Citric acid and its salts and/or sodium EDTA may also be included to increase stability. Antioxidizing agents, e.g., sodium bisulfite, sodium sulfite and/or ascorbic acid, either alone or in combination, are suitable stabilizing agents. In addition, the solutions may include pharmaceutically acceptable preservatives, e.g., benzalkonium chloride, methyl- or propyl-paraben, and/or chlorobutanol. Suitable pharmaceutical carriers are described in Remington's (supra).

In one embodiment, treatment of SOJIA includes administering an amount of at least one agent to significantly reduce or effectively block the transcription of the interleukin-1 beta (IL-1β) gene. Exemplary agents for the present invention suitable for blocking the transcription of the interleukin-1 beta (IL-1β) gene include but are not limited to anti-sense RNA compounds (Mehta R C, et al. 2000. "Intercellular adhesion molecule-1 suppression in skin by topical delivery of anti-sense oligonucleotides," *J Invest Dermatol* 115):805-812; Frankel A E, et al. 2001. "Novel therapeutics for chemotherapy-resistant acute myeloid leukaemia," *BioDrugs* 15:55-57; Lorenz H M and Kalden J R. 2001. "New therapy developments in rheumatoid arthritis," *Z Rheumatol* 60:326-32; Ideo G and Bellobuono A. 2002. "New therapies for the treatment of chronic hepatitis C," *Curr Pharm Des* 8:959-966; Sandborn W J and Targan S R. 2002. "Biologic therapy of inflammatory bowel disease," *Gastroenterology* 122:1592-1608).

In another embodiment, treatment of SOJIA includes administering an amount of at least one agent to significantly reduce or effectively block IL-1β receptors, including interleukin-1 receptor antagonist proteins or peptides. Exemplary agents for the present invention suitable for block IL-1β receptors include but are not limited to an isolated naturally occurring IL-1 receptor antagonist. One such agent is commercially available Anakinra (Kineret®, made by Amgen), a recombinant form of the naturally occurring IL-1 receptor antagonist.

In yet another embodiment, treatment of SOJIA includes administering an effective amount of at least one agent to significantly reduce or effectively block the release of IL-1β. Exemplary agents include anion transport inhibitors, lipoxins, and alpha-tocopherol. In yet another embodiment, treatment of SOJIA includes administering an effective amount of at least one agent to significantly reduce or effectively block the activity of IL-1β converting enzyme, a proteolytic enzyme that converts the inactive IL-1β precursor to its mature, active form. Exemplary agents include morphine and other opioids.

It is further contemplated that the present invention includes the administration of an antibody to IL-1β. The antibody to IL-1β can be made by any means known in the art. For example, monoclonal antibodies can be generated by immunizing mice with recombinant IL-1β or one or several synthetic peptides including epitopes that are regarded as highly antigenic. Alternatively, polyclonal antibodies can also be raised by immunizing rabbits using the above described antigens. The generated antibodies are examined to determine their ability to interact with IL-1 protein and their ability to block IL-1 mediated cellular responses. Once generated using hybridoma technology, the monoclonal antibodies are then humanized by swapping mouse and human framework and constant regions. According to the present invention, antibodies that block the biological effect of IL-1β block the IL-1-induced release of IL-8 from fibroblasts as described by Kaplanski G et al. 1994. "Interleukin-1 induces interleukin-8 secretion from endothelial cells by a juxtacrine mechanism," *Blood* 84:4242-4248. The IL-1β antibodies are then administered intravenously or subcutaneously to SOJIA patients in an effective amount to significantly reduce or effectively neutralize the biological function of IL-1β.

According to the present invention, the therapeutic response of SOJIA patients is monitored by assessing the patient's clinical improvement, i.e., disappearance and/or improvement of the fever, rash and arthritis, as well as normalization of the white blood cell count and the sedimentation rate.

Based on the finding that culturing SOJIA patient's sera with healthy blood mononuclear cells (PBMCs) in vitro results in significant induction of IL-1 beta (IL-1β) transcription (Example 1), two patients with persistently active disease for over 1 year in spite of more conventional aggressive treatment were treated with a commercially available anti-IL-1 medication (Anakinra, Amgen Inc., Thousand Oaks, Calif.), known to neutralize the biological activity of IL-1. As illustrated in Example 2 and 3, both patients became asymptomatic the day after initiation of therapy and remained asymptomatic for over 3 months.

EXAMPLE 1

Incubation of healthy PBMCs with SOJIA serum induces the transcriptional upregulation of Interleukin 1β. The gene expression profile was analyzed for healthy donor PBMCs before and after incubation with autologous serum or serum from two untreated and two treated SOJIA patients for six hours in vitro. After incubation with the serum, the PBMCs were processed to extract the RNA, and the RNA was hybridized to Affymetrix U133 A and B microarray chips. In this way, a wide array of genes whose transcription would be up-regulated or down-regulated with the SOJIA serum was screened.

Patient Population. PBMCs and sera from 23 SOJIA patients (15 females, 8 males, average age 7.1 years) fulfilling the ACR diagnostic criteria[34] were collected on repeated occasions. Patients were classified as active if they had systemic symptoms (fever and/or rash) and/or active arthritis (swollen and/or tender and limited joints). The control population consisted of 12 children (average 14 years) and 7 adults (average 35 years). The sera from healthy controls were cultured on repeated occasions with autologous and heterologous PBMCs. Patients and pediatric controls were recruited at Texas Scottish Rite Hospital for Children in Dallas. The study was approved by the Institutional Review Boards of UT Southwestern Medical Center, Texas Scottish Rite Hospital and Baylor Health Care System (IRB #0199017, 0701-513) and informed consent was obtained from parents or legal guardians.

PBMC cultures and RNA extraction. PBMCs were obtained by Ficoll-Histopaque gradient centrifugation of 20 ml of blood. PBMCs were cultured ($10^6$/ml) in RPMI 1640 supplemented with 20% autologous or SOJIA patient's serum for 6 hrs. RNA was extracted using RNAeasy kit (Qiagen, Valencia, Calif.) and assessed using an Agilent 2100 Bioanalyzer (Agilent, Palo Alto, Calif.). Supernatants were frozen at −80° C. PBMCs were cultured with RPMI 1640 and 10% fetal calf serum with PMA (50 ng/ml)-Ionomycin (1 µg/ml) for 24 hrs. Cells were harvested and the RNA extracted as above. Supernatants were frozen at −80° C.

Microarrays and Real-time PCR. Samples for microarray analysis were processed as described[18] and hybridized to the HG U133A Affymetrix GeneChip array containing 22,283 probe sets (Affymetrix Inc., Santa Clara, Calif.) at 45° C. for 16 hours. GeneChip arrays were washed stained and scanned according to protocols described in the GeneChip Expression Analysis Technical Manual (Affymetrix). Scanned GeneChips were visually inspected for abnormalities or irregularities.

Figure 1:
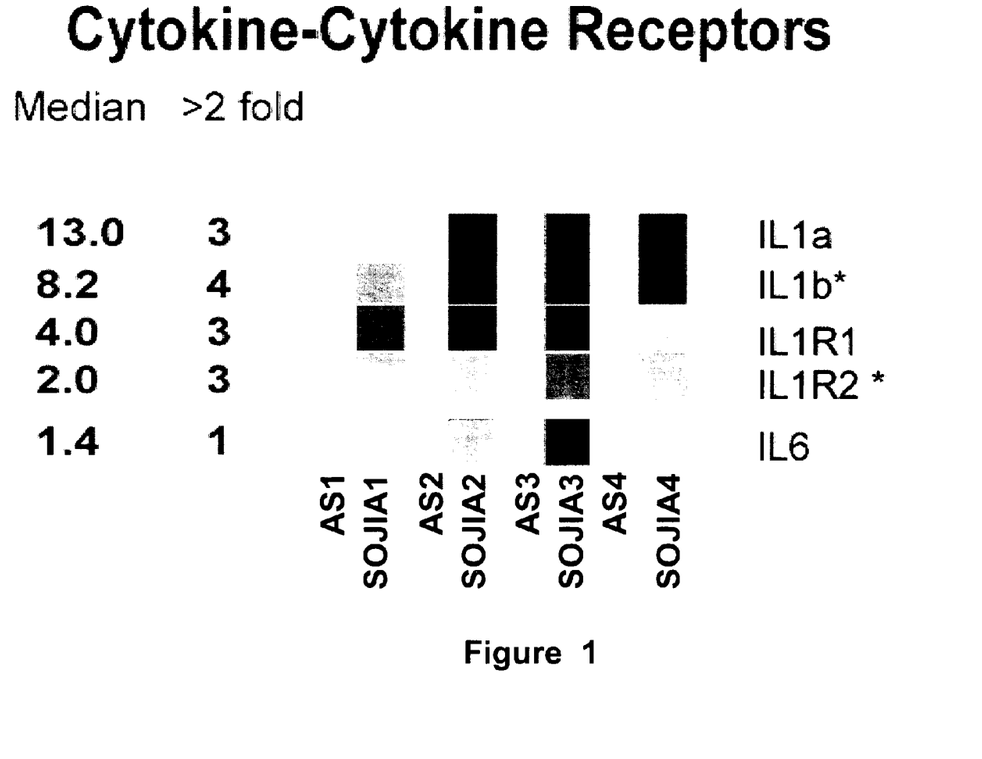
FIG. 1 is a graphic rendering of gene array data that depicts genes upregulated (red), downregulated (blue) or unchanged (yellow) upon incubation of PBMCs from four healthy volunteers with either autologous serum (AS) or the sera from three SOJIA patients.

FIG. 1 is a depiction of a gene array for cytokine-cytokine expression. Incubation of healthy PBMCs with autologous serum (AS) or with the serum from 4 SOJIA patients for 6 hr in vitro. SOJIA serum was found to induce the upregulation of transcription of members of the IL-1 family. Asterisk indicates that gene transcription is significantly upregulated in vivo in SOJIA patients PBMCs.

Data Analysis. Intensity values were scaled to 500 using global scaling in MAS 5.0 and data were exported in MS Excel for import into GeneSpring software (Silicon Genetics, Redwood City, Calif.) for gene expression analyses. No "per chip" normalization was performed as global scaling had been applied in MAS 5.0. Global scaling adjusts for chip-to chip variations in hybridization intensities. Subsequent samples were normalized to pediatric healthy controls and/or to the median of all samples. Statistical comparisons were performed in GeneSpring using both parametric (Welch's approximate t-test) and non-parametric (Mann-Whitney U-test) methods. Unsupervised hierarchical clustering was performed to visualize transcripts that had a control signal of 50 or above (above the background intensity) and that were identified as "present" according to MAS 5.0 in 15% of all samples. Statistical comparisons were performed in GeneSpring using both parametric (Welch's approximate t-test) and non-parametric (Mann-Whitney U-test) methods. Unsupervised hierarchical clustering was performed to visualize transcript/sample relationships using standard correlation, Pearson correlation or Euclidian distance where indicated.

Two-step RT-PCR was performed using Applied Biosystems TaqMan Assays on Demand probe and primer sets according to the manufacturer's instructions and the ABI Prism 7700 Sequence detection System (Applied Biosystems). The endogenous GAPDH gene and/or 18S RNA were used for correcting the results with the comparative threshold cycle ($C_T$) method for relative quantification as described by the manufacturer.

Multiplex Analysis (Luminex). Culture supernatants were analyzed for 6 cytokines and chemokines using the FluorikineMAP cytokine assay kit (R&D Systems, Minneapolis, Minn.) as per manufacturer's protocol.

Figure 2A:
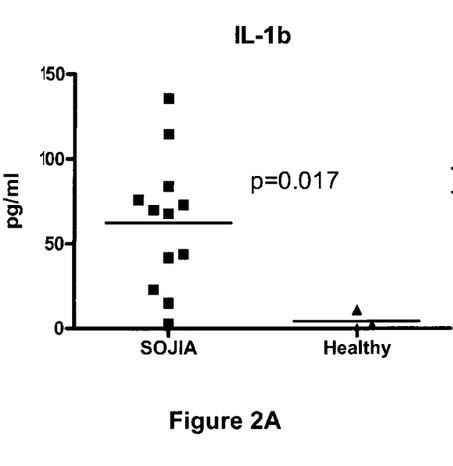
FIG. 2A is a graph that compares the induction of Interleukin 1-Beta (IL-b) protein secretion in healthy PBMCs incubated with SOJIA sera.

FIG. 2A is a graph that compares the induction of Interleukin 1-Beta (IL-b) protein secretion in healthy PBMCs incubated with SOJIA sera. Supernatants from 6 hr incubation of healthy PBMCs with 12 SOJIA sera and 3 healthy controls were assayed for IL-1b production by Luminex.

Figure 2B:
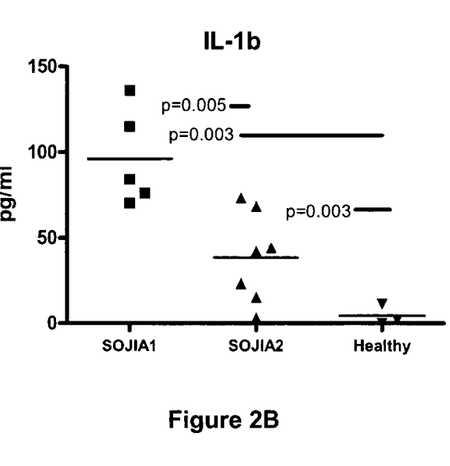
FIG. 2B is a graph that compares the induction of IL-1b protein secretion in SOJIA patients with and without systemic symptoms.

FIG. 2B is a graph that compares the induction of IL-1b protein secretion in SOJIA patients with and without systemic symptoms. IL-1b protein secretion is preferentially induced by sera from SOJIA patients experiencing systemic symptoms (SOJIA1, n=5) over those patients with only active arthritis (SOJIA2, n=7). All results were analyzed using non-parametric tests (Mann-Whitney).

Figure 3A:
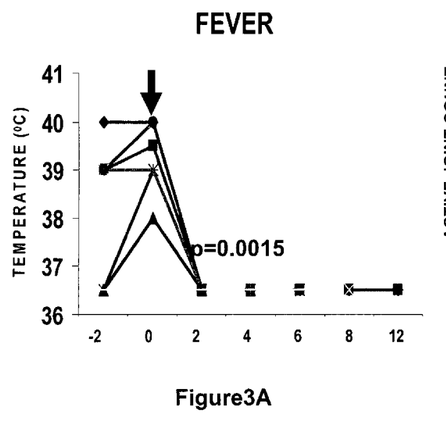
FIGS. 3A through F are graphs that shows the values of temperature (FIG. 3A); active joint count (FIG. 3B); WBC (FIG. 3C); hemoglobin (FIG. 3D); platelet count (FIG. 3E); and ESR in 9 SOJIA patients (FIG. 3F).
Figure 3B:
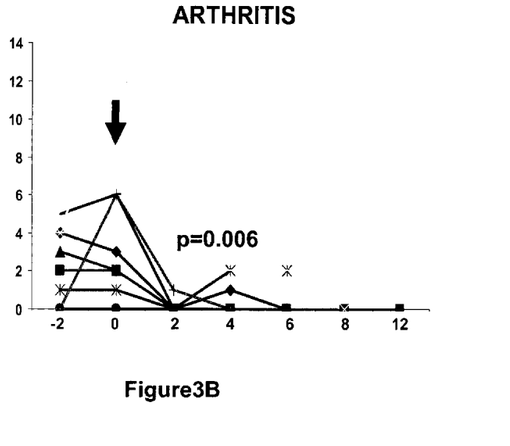
Figure 3C:
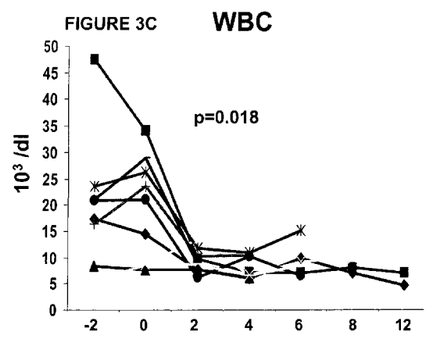
Figure 3D:
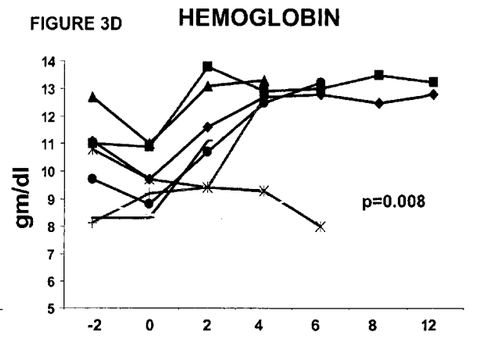
Figure 3E:
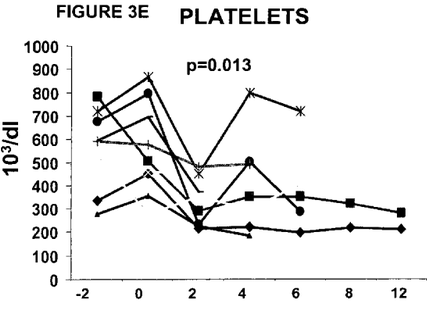
Figure 3F:
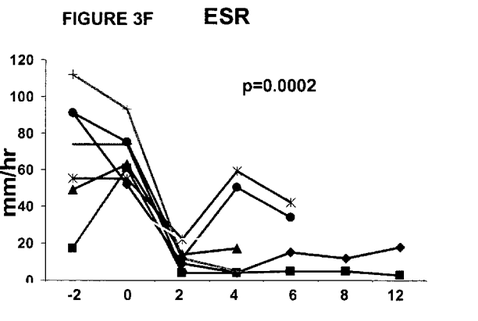

FIGS. 3A through F are graphs that shows the values of temperature (FIG. 3A); active joint count (FIG. 3B); WBC (FIG. 3C); hemoglobin (FIG. 3D); platelet count (FIG. 3E); and ESR in 9 SOJIA patients (FIG. 3F). X values represent months prior (−2) to starting of Anakinra treatment (0) and up to 2-12 months of follow up (average 6.6. months). Arrows

EXAMPLE 2

Interleukin 1β treatment of SOJIA patient. A 17 year old Hispanic female diagnosed with SOJIA at the age of 15 was treated according to the method of the present invention. She presented with persistent (>2 month) daily fever, a generalized pruritic rash and joint pain. On exam, she had swelling and limitation of the radio-carpal and carpal-metacarpal joints bilaterally. Her laboratory tests revealed high white blood cell count (WBC), low hemoglobin (Hgb), high platelets (Plts) and elevated erythrocyte sedimentation rate (ESR). An extensive infectious disease work up yielded negative results. The patient received oral and IV high dose methyl prednisolone and eventually was placed on methotrexate. Her symptoms improved, and the patient was asymptomatic for several months during which the steroid treatment was slowly tapered. A few months later the symptoms recurred. Steroids were reinitiated without success. Anti-TNF IV therapy (Infliximab) was tried at a dose of 5 mg/kg every month for approximately 6 months without any significant effect. After the patient had been symptomatic for over one year, IL-1 antagonist was administered in the form of Anakinra, 100 mg (1 cc) as a subcutaneous daily injection. The day after the first subcutaneous injection, the patient was asymptomatic, with the disappearance of fever, rash and joint swelling. Two follow-up visits confirmed that she remained asymptomatic at 2 and 3 months post-initiation of therapy. Laboratory tests also reflected this response, as WBC, Hgb, Plt number and ESR were within normal limits.

EXAMPLE 3

Interleukin 1β treatment of SOJIA patient. A 9 year old Hispanic male was diagnosed with SOJIA at the age of 7, when he presented with prolonged daily spiking fever, rash, pericarditis and joint and muscle pain. Laboratory tests showed high WBC, low Hgb, high platelets and elevated ESR. Bone marrow analysis and an extensive infectious work up failed to yield a specific diagnosis. The patient was treated with high dose IV methylprednisolone, and symptoms improved. Over the next two years, the patient presented flares and remissions. The last flare did not respond to high dose steroids, and the patient developed swelling over the radio-carpal joints bilaterally. Therapy with IL-1 antagonist Anakinra was initiated at a dose of 50 mg (0.5 cc) as a subcutaneous daily injection. The day after the first subcutaneous injection, the patient became asymptomatic, with the disappearance of fever, rash, joint pain and swelling, and he remained free of symptoms for over 3 months.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for treating a patient with systemic onset juvenile idiopathic arthritis (SOJIA) comprising:
    a) identifying a patient having symptoms of SOJIA; and
    b) administering to the patient a composition comprising a therapeutically effective amount to treat SOJIA of at least one active agent which reduces or blocks the interaction between interleukin-1β (IL-1β) and an IL-1 (IL-1) receptor wherein the active agent comprises an IL-1 receptor antagonist protein which binds to an IL-1 receptor, whereby a patient with SOJIA is therefore treated.

2. The method of claim 1, wherein the active agent comprises an anti-interleukin-1β receptor antibody which binds to an IL-1 receptor.

3. The method of claim 1, wherein the patient is asymptomatic from SOJIA after about 24 hours after treatment.

4. The method of claim 1, wherein the active agent comprises between about 1 to 250 mg per day.

* * * * *